US00PP07939P

United States Patent [19]

Nobbio

[11] Patent Number: Plant 7,939

[45] Date of Patent: Aug. 11, 1992

[54] CARNATION NAMED EPOMEO

[75] Inventor: Dott. G. Nobbio, San Remo, Italy

[73] Assignee: Selecta Klemm, Hanfacker, Fed. Rep. of Germany

[21] Appl. No.: 660,147

[22] Filed: Feb. 25, 1991

[51] Int. Cl.[5] ..... A01H 5/00

[52] U.S. Cl. ..... Plt./73.1

[58] Field of Search ..... Plt./71

[56] References Cited

U.S. PATENT DOCUMENTS

P.P. 5,767 7/1986 Nobbio ..... Plt. 71

*Primary Examiner*—James R. Feyrer

[57] ABSTRACT

A new standard carnation variety particularly distinguished by its continuous production of medium sized, Bright Red flowers during the mid season blooming period from Spring to Fall, the flowers being borne on long, sturdy, upright stems of a vigorous, upright bush of medium height which produces up to 8 stems per plant with a moderate amount of foliage and a vigorous upright growth habit having outstanding strength.

1 Drawing Sheet

BACKGROUND OF THE NEW PLANT

This new carnation cultivar originated as a seedling hybrid resulting from my crossing of the variety Ceriale (unpatented) by Chinera U.S. Plant Pat. No. 5,767 at my nursery at San Remo, Italy, the two varieties having been selected from my collection of breeding plants maintained at San Remo for breeding purposes. This particular seedling was selected for propagation because of its very nice Bright Red overall coloration and its apparently strong and vigorous growth habit and profuse production of blooms. Propagation of this selected seedling was done by me by means of cuttings at Sam Remo with such satisfactory results that further propagation by means of cuttings was carried on at Stuttgart, West Germany through several successive generations which proved conclusively that the novel characteristics of this new plant were retained from generation to generation and appeared to be fixed so that the homogeneity of the new plant could be assured for propagation of the plant on a commercial scale which is now being done at nurseries in Italy and Israel as well as in Germany.

DESCRIPTION OF THE DRAWING

This new carnation cultivar is illustrated by the accompanying photographic drawings which, in full color, shows several blooming stems including flowers at several stages of maturity with one of the stems showing one of the buds having burst into a full flower, the color rendition shown being as nearly true to that herein specified as is reasonably possible to obtain by conventional photographic procedures.

DESCRIPTION OF THE NEW PLANT

The following is a detailed description of my new standard carnation cultivar based upon observation of plants grown in greenhouse at the Selecta Klemm nursery at Stuttgart, West Germany, the color designations stated herein being according to The R.H.S. Color Chart published by The Royal Horticultural Society at London, England.

THE PLANT

Origin: Seedling.

Parentage:

*Seed parent.*—Carnation variety named Ceriale U.S. Plant Pat. No. 5,767.

*Pollen parent.*—Carnation variety named Chinera (unpatented). Both varieties are identified in my breeding records maintained at my nursery office at San Remo, Italy.

Classification:

*Botanic.*—*Dianthus caryophylus.*

*Commercial.*—Standard carnation.

Form: An erect and vigorous upright bush of outstanding strength and a height of about 90 to 100 cm.

Cane length: More than 60 cm.

Branching character: This bush produces many, up to eight, sturdy, upright branches emitted near the ground.

Foliage:

*Quantity.*—Moderate.

*Number of leaves.*—About 20 per plant.

*Size of leaf.*—Moderate.

*Shape.*—Oblong with entire margins.

*Texture.*—Smooth.

*Color.*—Upper side — Blue Green. Under side — Blue Green.

THE BUD

Size: Moderate.

*Diameter.*—About 20 mm.

*Length.*—About 30 mm.

Form: Ovoid.

Rate of opening: Moderate.

Color:

*When sepals first divide.*—Orient Red.

*When petals begin to unfurl.*—Orient Red.

Sepals:

*Number.*—5.

*Shape.*—Short, oblong with acute apex.

*Character.*—The sepals stand up when the flowers open.

*Color.*—Inside — Light Green. Outside — Green.

*Striae.*—Branching and Dark Green in color.

Calyx:
*Shape.*—Cylindrical.
*Size.*—Moderate, about 25 mm. wide and about 30 mm. long.
*Aspect.*—Smooth.
*Splitting.*—The calyx does not split.
Flower stem:
*Length.*—More than 60 cm.
*Character.*—Erect.
*Color.*—Blue Green.

THE FLOWER

Blooming habit: Continuous during mid season from Spring to Fall.
Size of bloom: Medium.
*Diameter.*—About 80 mm.
*Depth.*—About 30 to 35 mm.
Borne: Singly on strong upright stems.
Shape:
*When bloom first opens.*—Rounded upright center.
*When bloom matures.*—High center.
Petalage:
*Number of petals:* 50 to 60.
*Arrangement.*—Imbricated.
*Form.*—Oval with deeply serrated margins and ruffled apex.
*Texture.*—Soft.
*Appearance.*—Shiny.
*Color.*—Orient Red, RHS 44-B.
Flower stem:
*Length.*—More than 60 cm.
*Color.*—Blue Green.
*Character.*—Sturdy and upright.
Persistence: The petals hang on and dry and the bloom stays upright.

Fragrance: Weak.
Lasting quality:
*One plant.*—15 days.
*As cut flower.*—12 days.

THE REPRODUCTIVE ORGANS

Stamens:
*Number.*—Less than 10.
*Arrangement.*—Around the ovary.
*Anthers.*—Size: 4 mm. Color: Yellowish.
*Filaments.*—Length: 8 mm. Color: Yellowish.
*Pollen.*—Color: Yellow.
Pistils:
*Number.*—2.
*Styles.*—Length: 20 to 30 mm. Color: White.
*Stigmas.*—Color: White.
Character of the ovaries: Ovoid.

THE FRUIT

Fertility: The fruit is fertile.
Shape: Ovoid.
Color at maturity: Brown.

This plant ordinarily resembles those of the Chinera group and is particularly distinguished as a red seedling with deeply serrated petals and having high production due to the many stems per plant.

I claim:

1. The new and distinctive carnation cultivar, substantially as herein shown and described, particularly characterized by its high production of medium sized Orient Red flowers borne on long, strong, upright stems of the plant having many branches emitted near the ground and a moderate amount of foliage.

* * * * *

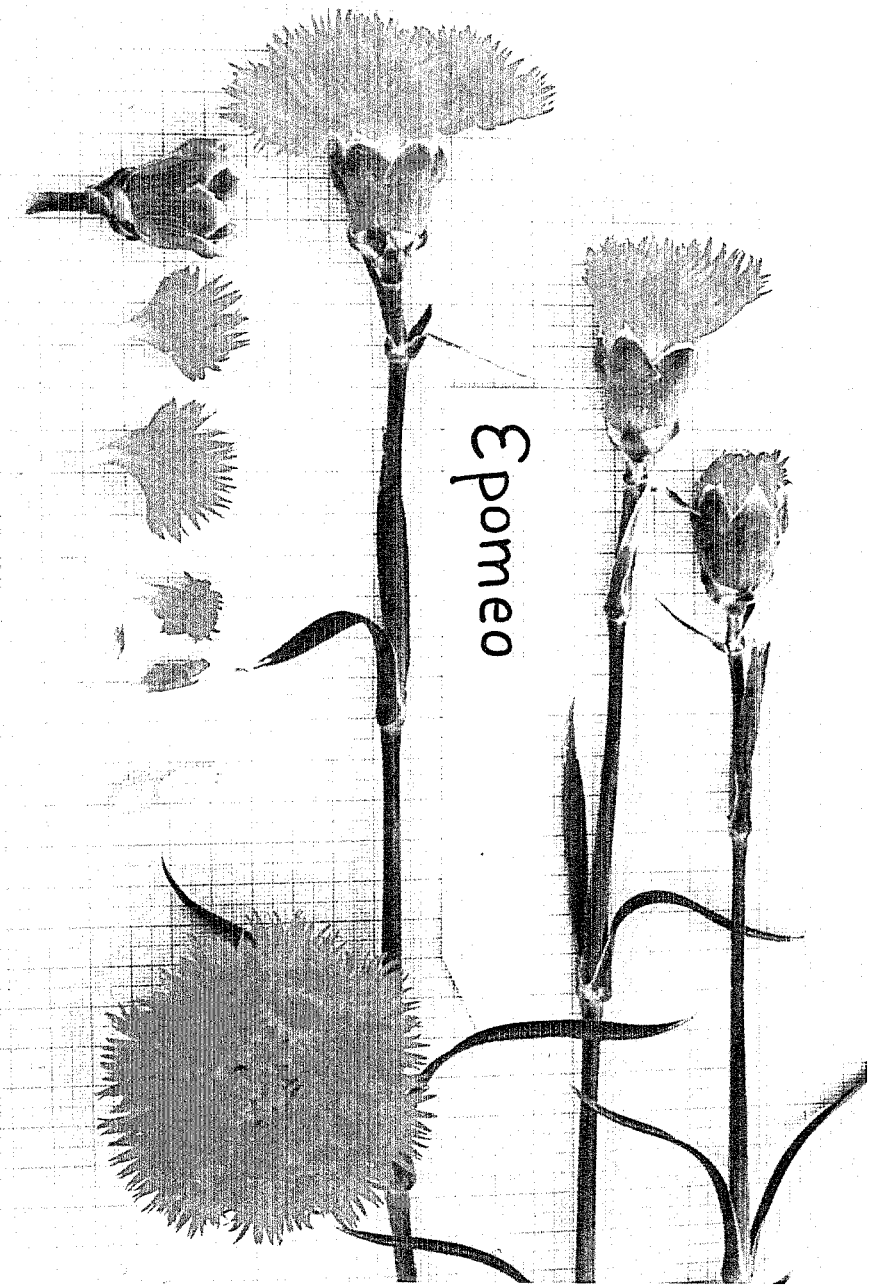
Epomeo

UNITED STATES PATENT AND TRADEMARK OFFICE

CERTIFICATE OF CORRECTION

PATENT NO. : Plant 7,939

DATED : August 11, 1992

INVENTOR(S) : Dott. G. Nobbio

It is certified that error appears in the above-identified patent and that said Letters Patent is hereby corrected as shown below:

Title page, column 2, line 6, delete "U.S. Plant Pat. No. 5,767" and insert --(Unpatented)

Title page, column 2, line 8, delete "(Unpatented)" and insert --U.S. Plant Pat. No. 5,767--.

Signed and Sealed this

Seventh Day of February, 1995

*Attest:*

Bruce Lehman

BRUCE LEHMAN

*Attesting Officer*

*Commissioner of Patents and Trademarks*